(12) United States Patent
Gutierrez et al.

(10) Patent No.: US 11,871,942 B1
(45) Date of Patent: Jan. 16, 2024

(54) ADJUSTABLE SURGICAL GUIDE

(71) Applicant: Glenoid Solutions, LLC, Tampa, FL (US)

(72) Inventors: Sergio Gutierrez, Tampa, FL (US); Jonathan Levy, Tampa, FL (US)

(73) Assignee: Glenoid Solutions, LLC, Tampa, FL (US)

( * ) Notice: Subject to any disclaimer, the term of this patent is extended or adjusted under 35 U.S.C. 154(b) by 0 days.

(21) Appl. No.: 18/240,217

(22) Filed: Aug. 30, 2023

(51) Int. Cl.
*A61B 17/17* (2006.01)
*A61B 17/56* (2006.01)
*A61B 17/00* (2006.01)

(52) U.S. Cl.
CPC .......... *A61B 17/17* (2013.01); *A61B 17/1778* (2016.11); *A61B 2017/00681* (2013.01); *A61B 2017/564* (2013.01)

(58) Field of Classification Search
CPC ..... A61B 17/17; A61B 17/1778; A61B 17/90; A61B 90/11
See application file for complete search history.

(56) References Cited

U.S. PATENT DOCUMENTS

| | | | | |
|---|---|---|---|---|
| 7,636,596 B2* | 12/2009 | Solar | ...................... | A61B 90/11 606/130 |
| 7,896,889 B2* | 3/2011 | Mazzocchi | ............ | A61B 90/11 606/130 |
| 8,315,689 B2* | 11/2012 | Jenkins | ................ | A61B 5/7435 600/410 |
| 8,500,743 B2* | 8/2013 | Birkbeck | ............. | A61B 17/175 269/6 |
| 9,498,297 B2* | 11/2016 | Yousef | .................... | A61B 34/71 |
| 2006/0229641 A1* | 10/2006 | Gupta | ................ | A61B 17/3403 606/130 |
| 2023/0132273 A1* | 4/2023 | Woodard | ........... | A61B 17/1775 606/87 |

* cited by examiner

Primary Examiner — Larry E Waggle, Jr.
(74) Attorney, Agent, or Firm — Foley & Lardner LLP

(57) ABSTRACT

A surgical guide includes a base and a drill guide coupled to the base. The drill guide includes a drill guide body defining a drill bore for receiving a drill bit and extending through the drill guide, the drill guide being configured to translate relative the base to adjust a drill guide angle defined by the drill bore and the base, the drill guide further being configured to transition between a locked state and an unlocked state, wherein the drill guide angle is fixed in the locked state and the drill guide angle is adjustable in the unlocked state.

25 Claims, 14 Drawing Sheets

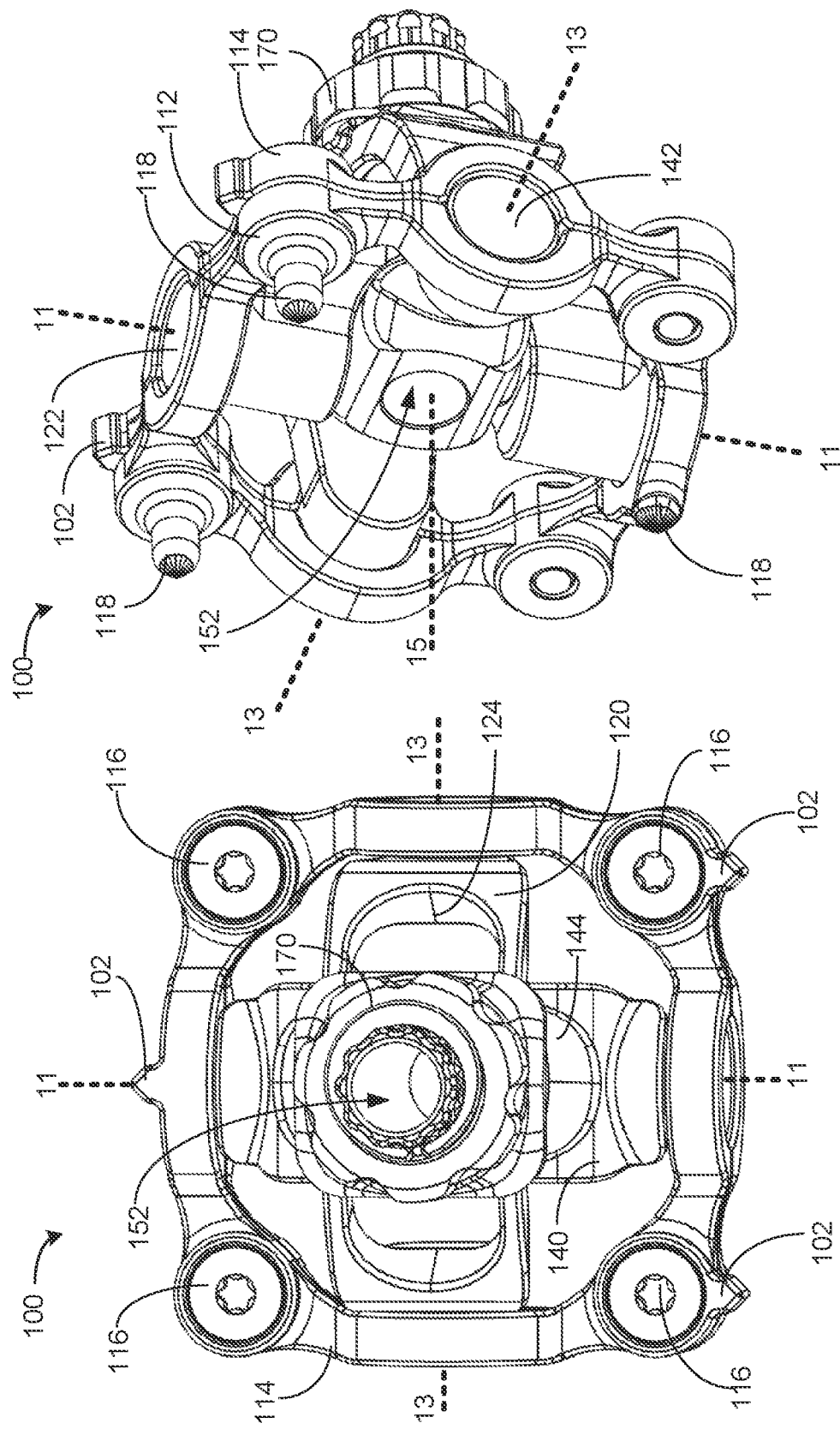

ADJUSTABLE SURGICAL GUIDE

FIELD

The present disclosure relates to apparatuses, systems, and methods for surgery. More particularly, the present disclosure relates to apparatuses, kits, systems, and methods of surgical guides.

BACKGROUND

Various types of surgical procedures involve removing tissue (e.g., bone, soft tissue, etc.) from a subject. For example, a surgical procedure may involve drilling into the subject. Surgical guides may be used to facilitate drilling into the subject.

SUMMARY

According to an aspect of the present disclosure, a surgical guide includes a base and a drill guide coupled to the base, the drill guide including a drill guide body defining a drill bore configured to receive a drill bit and extending through the drill guide, the drill guide being configured to translate relative the base to adjust a drill guide angle defined by the drill bore and the base, the drill guide further being configured to transition between a locked state and an unlocked state, wherein the drill guide angle is fixed in the locked state and the drill guide angle is adjustable in the unlocked state. According to various embodiments, the base includes a first foot including a first foot end, a second foot including a second foot end, and a third foot including a third foot end, wherein a base plane is defined by the first foot end, the second foot end, and the third foot end, the drill guide angle being defined by the drill bore and the base plane. According to various embodiments, the surgical guide includes a first track coupled to the base and defining a first track opening and a second track coupled to the base and defining a first track opening, and a second track coupled to the base and defining a second track opening, wherein the drill guide is configured to translate relative the base within the first track opening and the second track opening. According to various embodiments, the first track is rotatably coupled to the base and configured to rotate about a first axis. According to various embodiments, the first axis is parallel the base plane. According to various embodiments, the second track is rotatably coupled to the base and configured to rotate about a second axis. According to various embodiments, the second axis is perpendicular the first axis. According to various embodiments, the first axis and the second axis are parallel the base plane. According to various embodiments, drill guide includes a locking nut configured to rotate relative the drill bore, wherein rotation of the locking nut causes the drill guide to transition between the locked stated and the unlocked state. According to various embodiments, the drill guide further includes a clamping member, wherein the rotation of the locking nut in a first direction causes the clamping member to compress against the second track to secure the drill guide in the locked state. According to various embodiments, the drill guide further includes a first projection and a second projection extending from an outer portion of the drill guide body, wherein the rotation of the locking nut in the first direction causes the first projection and the second projection to compress against the first track to secure the drill guide in the locked state. According to various embodiments, the first track opening is a linear opening extending in a direction parallel to the base plane. According to various embodiments, the second track opening is a curved opening defining a convex curvature relative the base plane. According to various embodiments, the drill guide includes an adapter proximate a first end of the drill guide body, the adapter configured to receive a drill guide retainer. According to various embodiments, the adapter includes a plurality of spines surrounding an outer portion of the drill guide body.

According to another aspect of the present disclosure, a surgical system includes a surgical guide including a base and a drill guide coupled to the base, the drill guide including a drill guide body defining a drill bore configured to receive a drill bit and extending through the drill guide, the drill guide being configured to translate relative the base to adjust a drill guide angle defined by the drill bore and the base, the drill guide further being configured to transition between a locked state and an unlocked state, wherein the drill guide angle is fixed in the locked state and the drill guide angle is adjustable in the unlocked state. The surgical system further includes an adjustment device configured to cause a change in the drill guide angle. The adjustment device includes an adjustment base and a drill guide adjuster coupled to the adjustment base the drill guide adjuster including a handle proximate a first drill guide adjuster end of the drill guide adjuster, an adjustment projection proximate a second drill guide adjuster end of the drill guide adjuster, and a drill guide adjuster body positioned between the handle and the adjustment projection, the adjustment projection configured to be received within the drill bore such that movement of the handle causes a change in the drill guide angle. The surgical system further includes an adjustment stand configured to selectively coupled to the surgical guide, wherein the adjustment base is configured to receive at least a portion of the adjustment stand to limit relative movement between the adjustment base and the adjustment stand.

According to various embodiments, the drill guide adjuster further includes a first adjustment track coupled to the adjustment base and defining a first adjustment track opening and a second adjustment track coupled to adjustment body and defining a second adjustment track opening, wherein the drill guide adjuster, wherein movement of the handle causes the drill guide adjuster to translate within at least one of the first adjustment track opening or the second adjustment track opening. According to various embodiments, the first adjustment track is rotatably coupled to the adjustment base and configured to rotate about a first adjustment axis. According to various embodiments, the first adjustment axis is parallel a base plane defined by the base while the drill guide adjuster and the drill guide are coupled to the adjustment stand. According to various embodiments, the second adjustment track is rotatably coupled to the adjustment base and configured to rotate about a second adjustment axis. According to various embodiments, the second adjustment axis is perpendicular the first adjustment axis. According to various embodiments, rotation of the handle is configured to cause the drill guide to transition between the locked state and the unlocked state while the drill guide adjuster is coupled to the drill guide. According to various embodiments, the drill guide includes a locking nut configured to rotate relative the drill bore, wherein the rotation of the locking nut causes the drill guide to transition between the locked stated and the unlocked state. According to various embodiments, the locking nut includes a plurality of locking nut splines and the drill guide adjuster body includes a plurality of drill guide adjuster body splines configured to interface with the plurality of locking nut splines while the drill guide adjuster is coupled to the drill guide such that the rotation of the handle is configured to cause the drill guide to transition between the locked state and the unlocked state. According to various embodiments, the adjustment base defines an adjustment base plane and the drill guide adjuster includes a first adjustment track indicator configured to indicate a first relative angular orientation of the drill guide relative the adjustment base plane. According to various embodiments, the wherein the drill guide adjuster includes a second adjustment track indicator configured to indicate a second relative angular orientation of drill guide relative the adjustment base. According to various embodiments, the adjustment stand includes a first clamping arm and a second clamping arm configured to selectively coupled to the surgical guide to the adjustment stand.

According to another aspect of the present disclosure, a method includes providing an adjustment stand, coupling a surgical guide to the adjustment stand. The surgical guide includes a base, and a drill guide coupled to the base, the drill guide including a drill guide body defining a drill bore and extending through the drill guide, the drill bore and the base defining a drill guide angle. The method further includes providing an adjustment device. The adjustment device includes a drill guide adjuster coupled to the base, the drill guide adjuster including a handle proximate a first drill guide adjuster end of the drill guide adjuster, an adjustment projection proximate a second drill guide adjuster end of the drill guide adjuster, and a drill guide adjuster body positioned between the handle and the adjustment projection. The method further includes inserting the adjustment projection into the drill bore. The method further includes adjusting a position of the handle thereby causing the drill guide to translate relative the base to adjust the drill guide angle. The method further includes locking the drill guide such that the drill guide angle is fixed.

According to various embodiments, the method includes removing the adjustment projection from the drill bore, decoupling the drill guide from the adjustment stand, and providing the drill guide in a desired location proximate a bone. According to various embodiments, the method includes rotating the handle while the adjustment projection is positioned within the drill guide causing the drill guide to transition to a locked state to prevent change in the drill guide angle.

This summary is illustrative only and should not be regarded as limiting.

BRIEF DESCRIPTION OF THE DRAWINGS

FIG. 3 is another perspective view of the surgical guide of FIG. 1.

FIG. 4 is another perspective view of the surgical guide of FIG. 1.

DETAILED DESCRIPTION

Figures 1, 2:
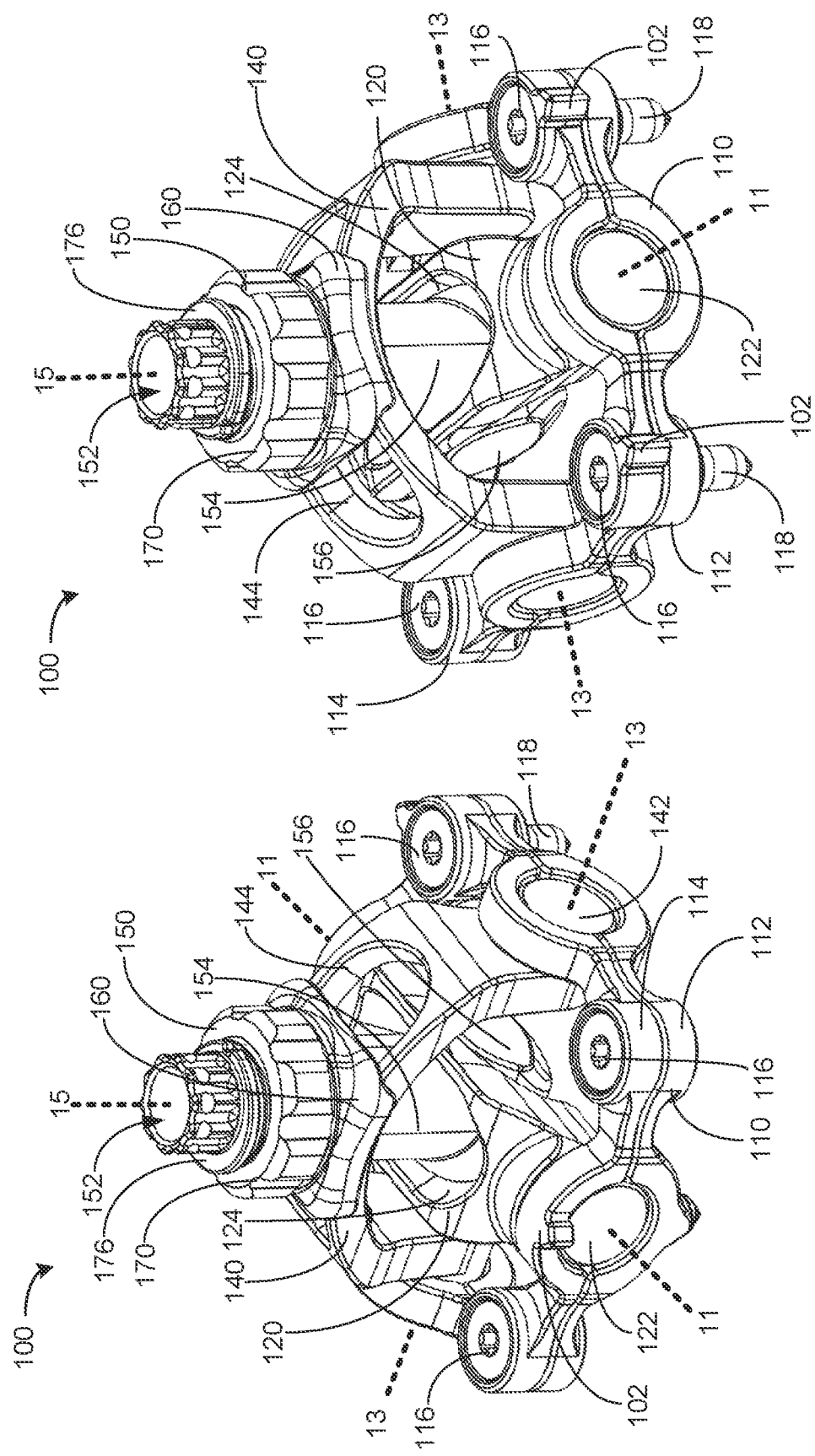
FIG. 1 is a perspective view of a surgical guide, according to an example embodiment.
FIG. 2 is another perspective view of the surgical guide of FIG. 1.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

The use of "e.g." "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "attached" and "coupled" and grammatically related terms refers to the fixed, releasable, or integrated association of two or more elements and/or devices with or without one or more other elements in between. Thus, the term "attached" or "coupled" and grammatically related terms include releasably attaching or fixedly attaching two or more elements and/or devices in the presence or absence of one or more other elements in between.

Surgical procedures can involve removing tissue (e.g., bone, soft tissue, etc.) from a subject. For example, a surgical procedure may involve drilling into the tissue the subject. Drilling into the tissue of the subject may involve drilling through a surgical guide, which may guide a drill bit into a desired location at a desired orientation. While surgical guides can improve accuracy of the drilling, the surgical guide may need to be specific to the subject of the surgical procedure. For example, due to various factors (e.g., the anatomy of the subject, the severity or type of injury being addressed, the condition of the tissue being drilled into, etc.), the surgical guide may need to be specific for the surgical procedure and the subject for optimal results. However, creating a custom surgical guide for each procedure may be a timely and expensive process.

Referring to the figures generally, a surgical guide is shown, according to an example embodiment. The surgical guide is configured to be quickly and easily adjusted (e.g., using an adjustment stand and a drill guide adjuster) such that tissue may be removed in a desired location and at a desired orientation (e.g., angle). For example, a desired or optimal drill angle (e.g., a desired orientation of a hole being drilled into a bone of the subject relative a surface of the bone) may be determined prior to the procedure and a user of the surgical guide may set a drill guide angle (e.g., an angle defined by a drill bore of the drill guide and a base plane defined by a base of the surgical guide) based on the optimal drill angle. The surgical guide may then be positioned in a desired location proximate the tissue of the subject and a hole may be drilled through the drill bore of the surgical guide.

According to various embodiments, the drill guide is reusable. For example, the drill guide may be formed of a material that will not deteriorate during a sanitation process (e.g., within an autoclave). Thus, the drill guide may be customizable for a desired procedure and reusable to reduce cost. Additionally, or alternatively, one or more of the other components of the surgical systems described herein may be reusable (e.g., the drill guide adjustor and/or the adjustment stand).

According to various embodiments described herein, a surgical guide includes a base defining a base plane. The base may be configured to engage tissue of a subject of a surgical procedure. The surgical guide further includes a first track coupled to the base and defining a first track opening and a second track coupled to the base and defining a second track opening. A drill guide may be coupled to at least one of the first track or the second track. For example, the drill guide may extend through the first track opening and the second track opening such that movement of the drill guide is restricted by the first track and/or the second track. The drill guide may include a drill guide body defining a drill bore that extends along a drill bore axis through the drill guide body. The drill bore may be configured to receive a drill bit such that the drill bit can be inserted through the drill guide to remove tissue from the subject. The drill guide may be configured to translate relative the base within the first track opening and the second track opening to adjust a drill guide angle defined by the drill bore and the base plane. For example, a user of the drill guide may change the drill guide angle based on a determined optimal drill angle prior to drilling through the drill guide.

According to various embodiments, the base includes a first foot including a first foot end, a second foot including a second foot end, and a third foot including a third foot end, wherein the base plane is defined by the first foot end, the second foot end, and the third foot end. Each of the first foot end, the second foot end, and the third foot end may come to a pointed end such that the base plane extends through each of the pointed ends.

According to various embodiments, the first track is rotatably coupled to the base and configured to rotate about a first axis. The first axis may be parallel the base plane. The second track is rotatably coupled to the base and configured to rotate about a second axis. The second axis may be perpendicular the first axis. Further, the first axis and the second axis may be parallel the base plane.

According to various embodiments, the drill guide is configured to transition between a locked state and an unlocked state. The drill guide angle may be fixed (e.g., locked, restricted, etc.) in the locked state and the drill guide angle may be adjustable in the unlocked state. The drill guide may include a locking nut configured to rotate relative the drill bore, wherein rotation of the locking nut causes the drill guide to transition between the locked stated and the unlocked state. The drill guide further may include a clamping member configured to secure the drill guide in the locked state. For example, rotation of the locking nut in a first direction may cause the clamping member to compress against the second track to secure the drill guide in the locked state. The drill guide further may further include a first projection and a second projection extending from an outer portion of the drill guide body. The rotation of the locking nut in the first direction may causes the first projection and the second projection to compress against the first track (e.g., in an opposite direction as the clamping member) to further secure the drill guide in the locked state.

According to various embodiments, the first track opening is a linear opening extending in a direction parallel to the base plane. Further, the second track opening may be a curved opening defining a convex curvature relative the base plane.

According to various embodiments, the drill guide includes an adapter proximate a first end of the drill guide body. The adapter may be configured to receive a drill guide retainer or a drill guide reducer. The adapter may include a plurality of spines surrounding an outer portion of the drill guide body.

According to various embodiments, a surgical system includes surgical guide. The surgical guide may include a base defining a base plane, a first track coupled to the base and defining a first track opening, a second track coupled to the base and defining a second track opening, and a drill guide coupled to at least one of the first track or the second track and extending through the first track opening and the second track opening. The drill guide may include a drill guide body defining a drill bore configured to receive a drill bit. The drill guide may be configured to translate relative the base within the first track opening and the second track opening to adjust a drill guide angle defined by the drill bore and the base plane.

According to various embodiments, the surgical system includes an adjustment device configured to cause a change in the drill guide angle. The adjustment device may include one or more angular indicators configured to provide visual feedback to a user of the adjustment device, thereby allowing the user to precisely set the desired drill guide angle. The adjustment device may include an adjustment base, a first adjustment track coupled to the adjustment base and defining a first adjustment track opening, a second adjustment track coupled to adjustment body and defining a second adjustment track opening, and a drill guide adjuster coupled to at least one of the first adjustment track or the second adjustment track. The drill guide adjuster may extend through the first adjustment track opening and the second adjustment track opening. The drill guide adjuster may include a handle proximate a first drill guide adjuster end of the drill guide adjuster. The drill guide adjuster may include an adjustment projection proximate a second drill guide adjuster end of the drill guide adjuster, and a drill guide adjuster body positioned between the handle and the adjustment projection. The adjustment projection may be configured to be received within the drill bore such that movement of the handle causes a change in the drill guide angle, thereby allowing the user of the adjustment device to adjust the drill guide angle.

According to various embodiments, the surgical system includes an adjustment stand. The adjustment stand may be configured to selectively coupled to the surgical guide.

Further, the adjustment base may be configured to receive at least a portion of the adjustment stand to limit relative movement between the adjustment base and the adjustment stand. For example, the adjustment device may be placed on top of the adjustment stand and a portion of the adjustment stand base may be contained within the adjuster base to prevent relative movement therebetween.

According to various embodiments, the first adjustment track is rotatably coupled to the adjustment base and configured to rotate about a first adjustment axis. The first adjustment axis may be parallel to the base plane while the drill guide adjuster and the drill guide are coupled to the adjustment stand. The second adjustment track may be rotatably coupled to the adjustment base and configured to rotate about a second adjustment axis. The second adjustment axis may be perpendicular to the first adjustment axis.

According to various embodiments, the drill guide is configured to transition between a locked state and an unlocked state, wherein the drill guide angle is fixed in the locked state and the drill guide angle is adjustable in the unlocked state. When the adjustment projection is positioned within the drill bore, rotation of the handle may to cause the drill guide to transition between the locked state and the unlocked state. For example, the drill guide may include a locking nut configured to rotate relative the drill bore, wherein the rotation of the locking nut causes the drill guide to transition between the locked stated and the unlocked state. The locking nut may include a plurality of locking nut splines and the drill guide adjuster body includes a plurality of drill guide adjuster body splines configured to interface with the plurality of locking nut splines while the drill guide adjuster is coupled to the drill guide such that the rotation of the handle is configured to cause the drill guide to transition between the locked state and the unlocked state.

According to various embodiments, the first adjustment track opening is a linear opening, and the second track opening is a curved opening defining a convex curvature. The adjustment base may define an adjustment base plane and the drill guide adjuster includes a first adjustment track indicator configured to indicate a first relative angular orientation of the drill guide (e.g., within a first adjustment plane) relative the adjustment base plane. The drill guide adjuster may include a second adjustment track indicator configured to indicate a second relative angular orientation of the drill guide (e.g., within a second adjustment plane) relative the adjustment base. The adjustment stand may include a first clamping arm and a second clamping arm configured to selectively coupled to the surgical guide to the adjustment stand.

According to various embodiments, a method of using a surgical guide includes providing an adjustment stand and coupling a surgical guide to the adjustment stand. The surgical guide may include a base defining a base plane, a first track coupled to the base and defining a first track opening, a second track coupled to the base and defining a second track opening, and a drill guide coupled to at least one of the first track or the second track and extending through the first track opening and the second track opening. The drill guide may include a drill guide body defining a drill bore and extending through the drill guide, the drill bore and the base plane defining a drill guide angle. The method may further include providing an adjustment device. The adjustment device may include an adjustment base, a first adjustment track coupled to the adjustment base and defining a first adjustment track opening, a second adjustment track coupled to adjustment body and defining a second adjustment track opening, and a drill guide adjuster coupled to at least one of the first adjustment track or the second adjustment track and extending through the first adjustment track opening and the second adjustment track opening. The drill guide adjuster may include a handle proximate a first drill guide adjuster end of the drill guide adjuster, an adjustment projection proximate a second drill guide adjuster end of the drill guide adjuster, and a drill guide adjuster body positioned between the handle and the adjustment projection. The method may further include inserting the adjustment projection into the drill bore and adjusting a position of the handle thereby causing the drill guide to translate relative the base within the first track opening and the second track opening to adjust the drill guide angle.

According to various embodiments, the method further includes removing the adjustment projection from the drill bore, decoupling the drill guide from the adjustment stand, and providing the drill guide in a desired location proximate a bone. The method may further include rotating the handle while the adjustment projection is positioned within the drill guide causing the drill guide to transition to a locked state to prevent change in the drill guide angle.

Referring now to FIGS. 1-4, perspective views of a surgical guide 100 are shown, according to an example embodiment. The surgical guide 100 is configured to be adjusted such that a hole can be drilled into a subject at a desired drill angle. The surgical guide 100 includes a base 110 that defines a base plane. For example, the base 110 may include a first foot 118, a second foot 118, and a third foot 118 that define the base plane. As shown, the first foot 118, the second foot 118, and the third foot 118 each come to a pointed foot end. The base plane may be a plane that intersects all three of the pointed foot ends.

The base 110 further includes a first base plate 112 and a second base plate 114 coupled to the first base plate 112 via a plurality of fasteners 116. As is discussed further herein, the first base plate 112 and the second base plate 114 define a plurality of apertures configured to each individually receive a first track projection 122 of a first track 120 of a second track projection 142 of a second track 140, thereby coupling the first track 120 and the second track 140 to the base 110. The second base plate 114 is shown to include a plurality of indicators 102. The indicators 102 may provide visual feedback to a user of the surgical guide 100 to allow them to properly orientate the surgical guide 100.

The surgical guide 100 includes the first track 120. As discussed above, the first track 120 includes a first track projections 122 that are received between the first base plate 112 and the second base plate 114. The first track projections 122 allow the first track 120 to rotate about a first axis 11 relative the base 110. For example, the first track 120 may rotate about the first axis 11 as a user of the surgical guide 100 sets a desired drill guide angle, as is discussed further herein. The first track 120 further includes a first track opening 124 extending through the first track 120. The first track opening 124 is configured to receive a portion of a drill guide 150 and allows a portion of the drill guide 150 to translate within the first track opening 124 as a user of the surgical guide 100 sets a desired drill guide angle. As shown, the first track opening 124 is generally linear in nature. For example, the first track opening 124 may extend in a direction parallel to the base plane.

The surgical guide 100 includes the second track 140. As discussed above, the second track 140 includes a second track projections 142 that are received between the first base plate 112 and the second base plate 114. The second track projections 142 allow the second track 140 to rotate about a second axis 13 relative the base 110. For example, the second track 140 may rotate about the second axis 13 as a user of the surgical guide 100 sets a desired drill guide angle, as is discussed further herein. The first axis 11 and the second axis 13 may be perpendicular one another and/or parallel the base plane. The second track 140 further includes a second track opening 144 extending through the second track 140. The second track opening 144 is configured to receive a portion of a drill guide 150 and allows a portion of the drill guide 150 to translate within the second track opening 144 as a user of the surgical guide 100 sets a desired drill guide angle. As shown, the second track opening 144 is generally arced in nature. For example, the second track opening 144 may extend at a curvature that defines a convex curvature relative the base plane.

The surgical guide 100 further includes a drill guide 150 coupled to the first track 120 and the second track 140. The drill guide 150 includes a drill bore 152 extending along a bore axis 15 from a first end of the drill guide 150 to a second end of the drill guide 150. The drill bore 152 is configured to receive a portion of a drill (e.g., a drill bit), such that a hole can be drilled through the drill bore 152. The drill guide 150 further includes a drill guide body 154 between the first end and the second end of the drill guide 150. The drill guide body 154 is configured to translate within the first track opening 124 and the second track opening as user of the surgical guide 100 sets a desired drill guide angle. The drill guide angle may be defined as the angle formed by the bore axis 15 and the base plane.

The drill guide 150 further includes a locking nut 170. As discussed further herein, the locking nut 170 is configured to be rotated to transition the surgical guide 100 from a locked state to an unlocked state. For example, rotation of the locking nut 170 in a first direction (e.g., relative the bore axis 15) may cause a clamping member 160 to compress against the second track 140 to secure the drill guide 150 in the locked state, such that the drill guide angle is fixed.

The drill guide further includes a retention member 176. The retention member 176 is configured to limit translation of the locking nut 170 along the drill guide 150. For example, the locking nut 170 may be rotated to unlock the drill guide 150. The locking nut 170 may engage the retention member 176 as the locking nut 170 is rotated to or past the unlocked position. Thus, the locking nut 170 may prevent the retention member 176 from being over rotated past the unlocked position, as is discussed further herein.

The drill guide 150 further includes projections 156 extending from the drill guide body 154 proximate the second end of the drill guide 150. As is discussed further herein, the projections 156 are configured to engage the first track 120 to secure the drill guide 150 in the locked state. For example, the projections 156 may compress against the first track 120 (e.g., in a direction opposite the compression of the clamping member 160 against the second track) in response to the locking nut 170 being rotated, to secure the drill guide 150 in the locked state, such that the drill guide angle is fixed.

Figure 6:
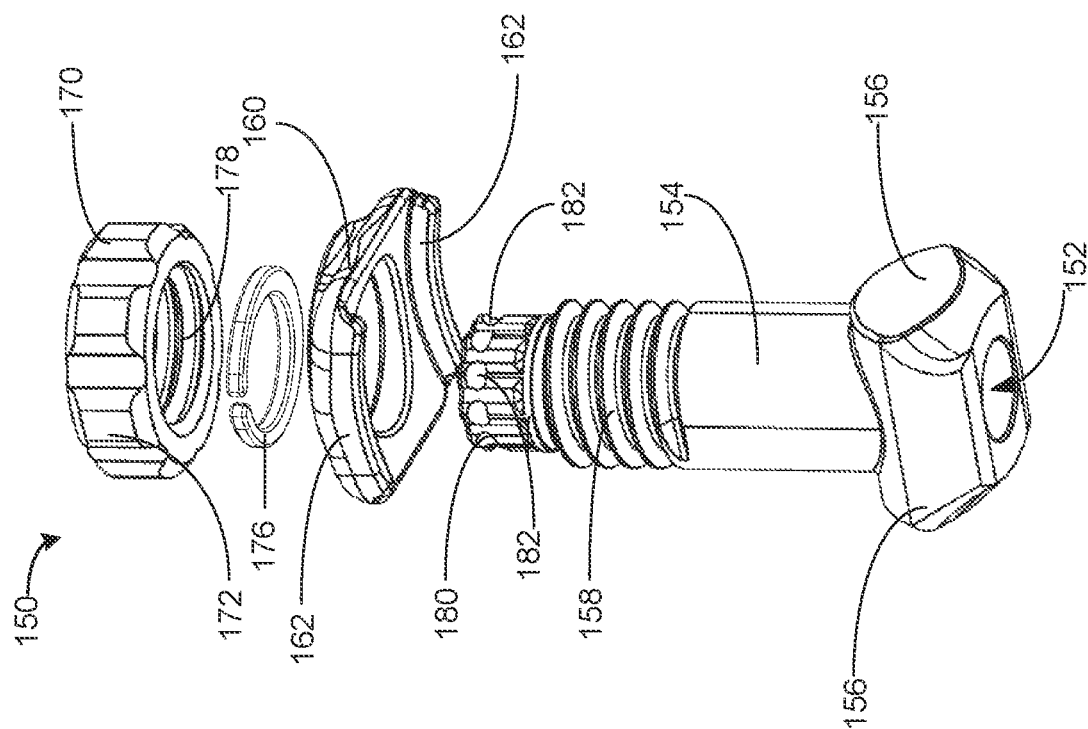
FIG. 6 is an exploded view of the drill guide body of FIG. 5.
Figure 5:
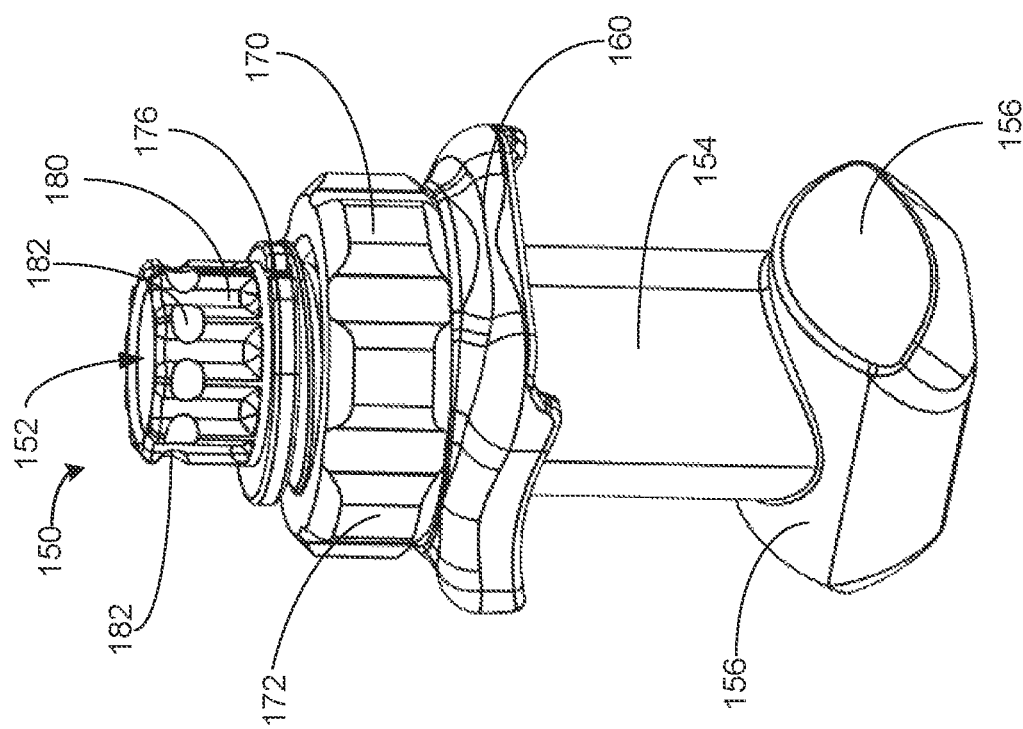
FIG. 5 is a perspective view of a drill guide body, according to an example embodiment.

Referring not to FIGS. 5 and 6, a perspective view and an exploded view of the drill guide 150 are shown, respectively, according to an example embodiment. The drill guide 150 includes the drill bore 152 extending through the drill guide body 154. The drill guide body 154 further includes a plurality of threads 158 configured to interface with a plurality of threads 178 on an inner portion of the locking nut 170. As the locking nut 170 is rotated in a first direction, the locking nut 170 translates along the drill guide body 154, thereby compressing the clamping member 160 in a first clamping direction against the second track 140 (see FIGS. 1 and 2). As the locking nut 170 is rotated in a second direction (e.g., opposite the first direction), the drill guide 150 transition to the unlocked state. As the locking nut 170 continues to rotate in the second direction, the locking nut 170 will engage the retention member 176 to prevent over-rotation of the locking nut 170. For example, the retention member 176 may prevent the threads 178 of the locking nut 170 from disengaging the plurality of threads 158 on the drill guide body 154.

Further, the projections 156 may compress against the first track 120 in a second clamping direction, opposite the first clamping direction, in response to the locking nut 170 being rotated in the first direction to secure the drill guide 150 in the locked state, such that the drill guide angle is fixed. The locking nut 170 includes a plurality of splines 172 configured to interface with a plurality of splines (e.g., splines 356 in FIG. 10) to facilitate rotation of the locking nut 170 via an adjustment device.

The clamping member 160 further includes a pair of rails 162 on opposite lateral sides of the clamping member 160. The rails 162 are configured to engage the second track 140 (see FIGS. 1 and 2) as the drill guide 150 translates within the second track opening 144 to restrict relative movement between the drill guide 150 and the second track 140.

The drill guide 150 further includes an adapter 180 proximate the first end of the drill guide 150. The adapter 180 includes a plurality of splines and is configured to couple the drill guide 150 to a drill guide retainer or a drill guide reducer, as is discussed further with respect to FIGS. 15-17. The adapter 180 further includes a plurality of indents 182 configured to engage one or more projections of a drill guide retainer, as is discussed further below with respect to FIG. 17.

Figure 7:
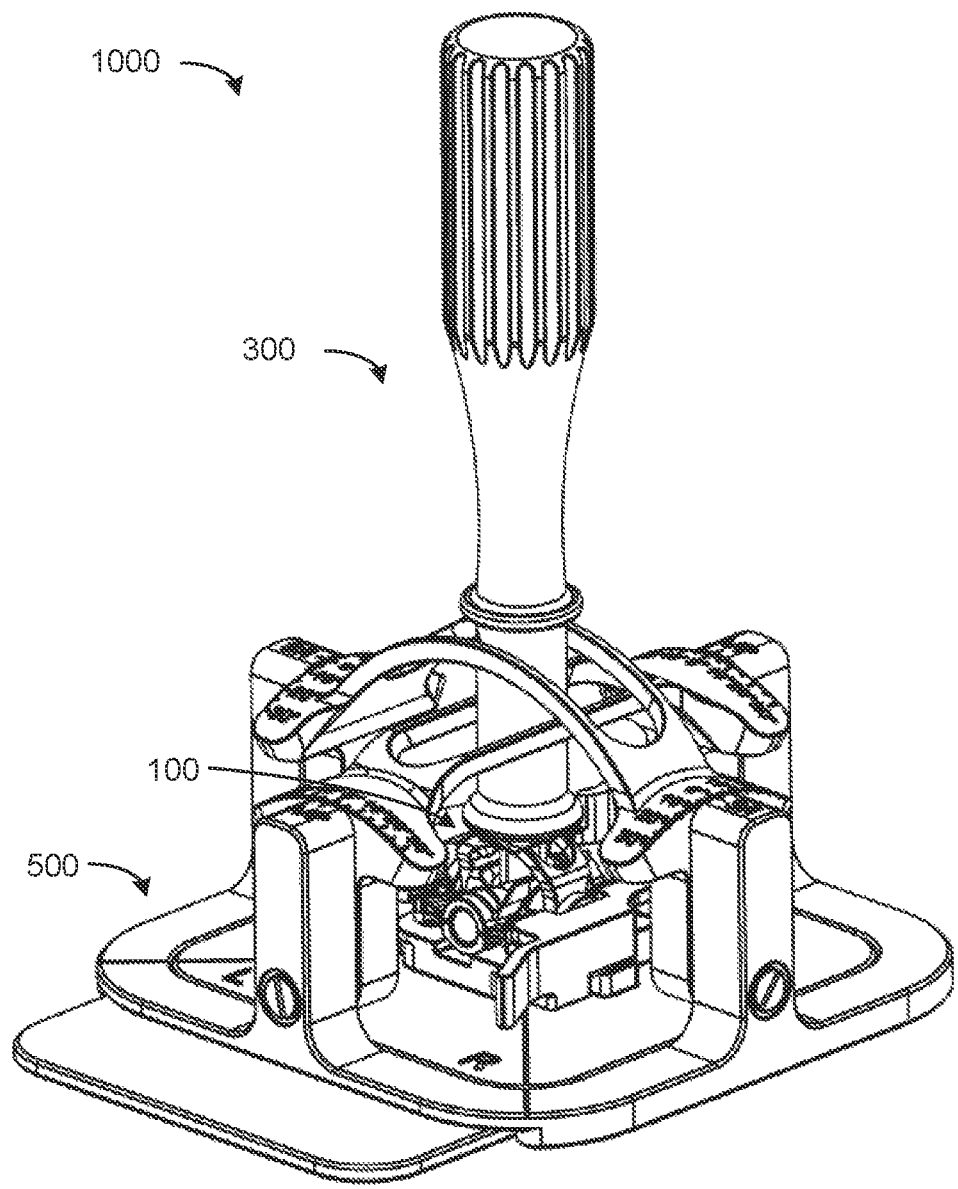
FIG. 7 is a perspective view of a surgical system, according to an example embodiment.
Figure 8:
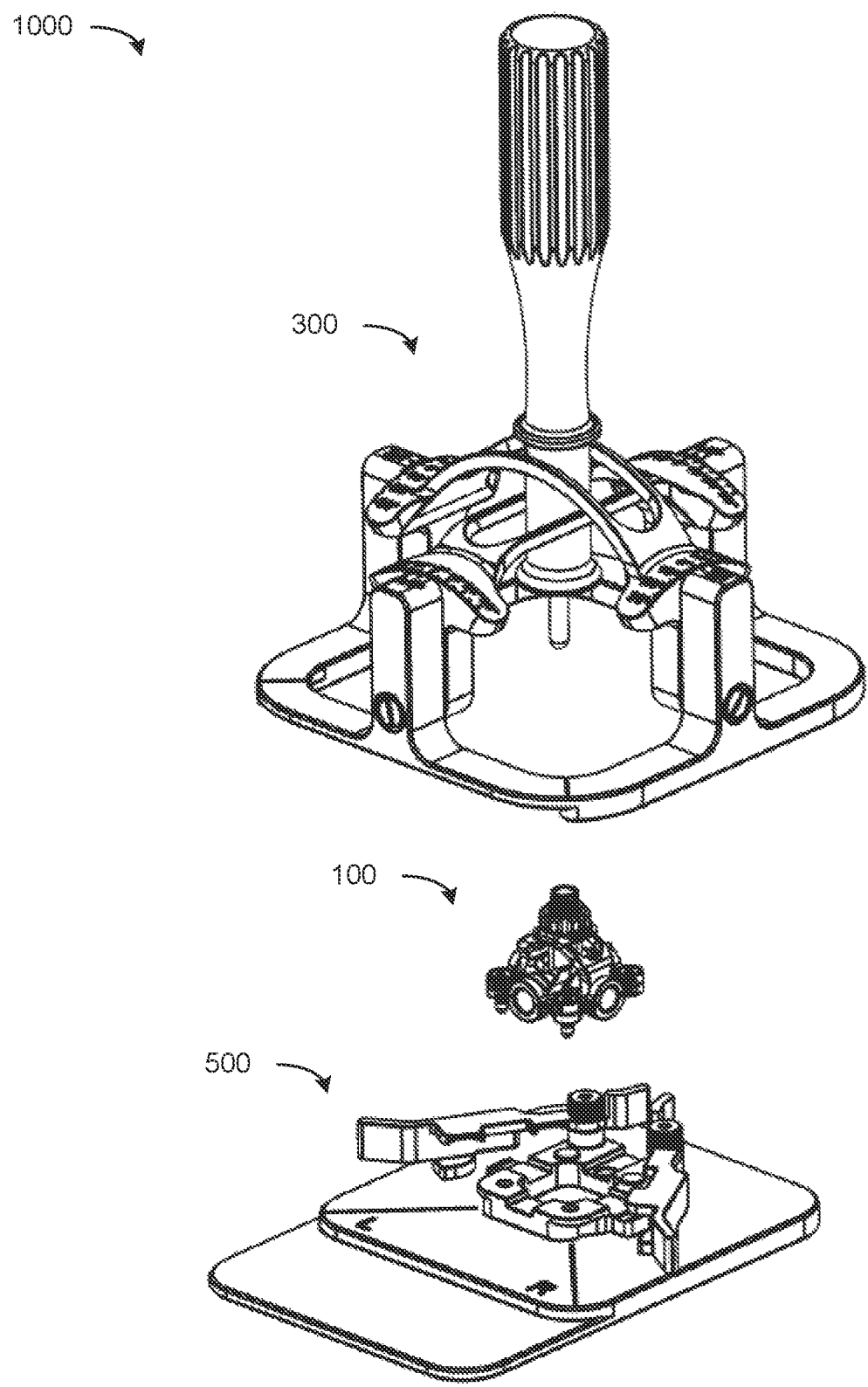
FIG. 8 is an exploded view of the surgical system of FIG. 7.

Referring now to FIGS. 7 and 8, a perspective view and an exploded view of a surgical system 1000 are shown, respectively, according to an example embodiment. The surgical system 1000 includes the surgical guide 100, an adjustment device 300, and an adjustment stand 500. As is discussed further herein, the adjustment stand 500 is configured to support (e.g., receive, couple with, etc.) the surgical guide 100. The adjustment stand 500 can then be positioned on top of the adjustment stand 500 such that the surgical guide 100 is positioned between a portion of the adjustment device 300 and a portion of the adjustment stand 500. The adjustment device 300 can then be used to lock and/or unlock the surgical guide 100 and/or adjust a drill guide angle of the drill guide 150.

Figure 10:
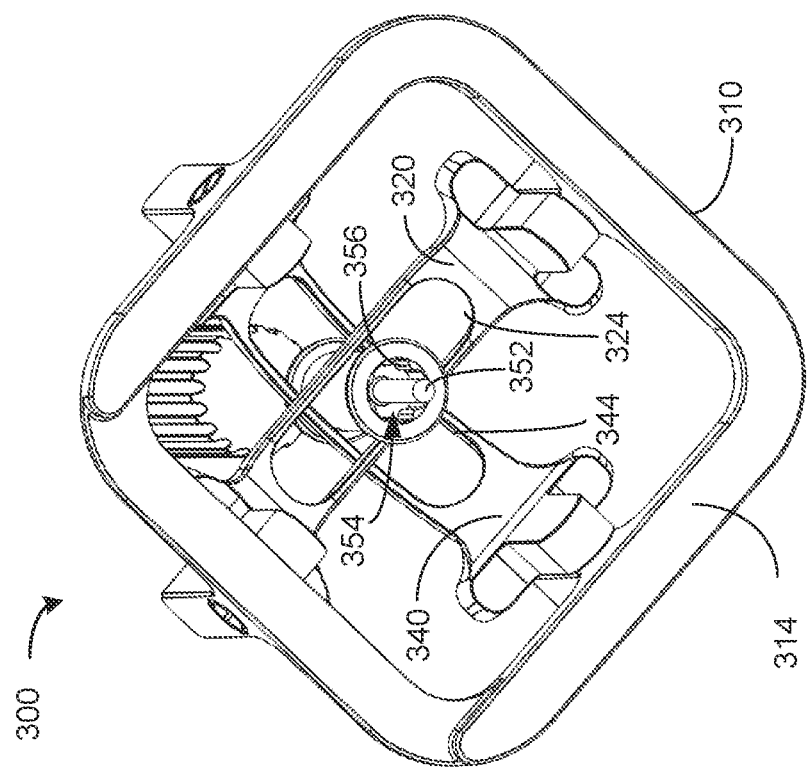
FIG. 10 is another perspective view of the drill guide adjuster of FIG. 9.
Figure 9:
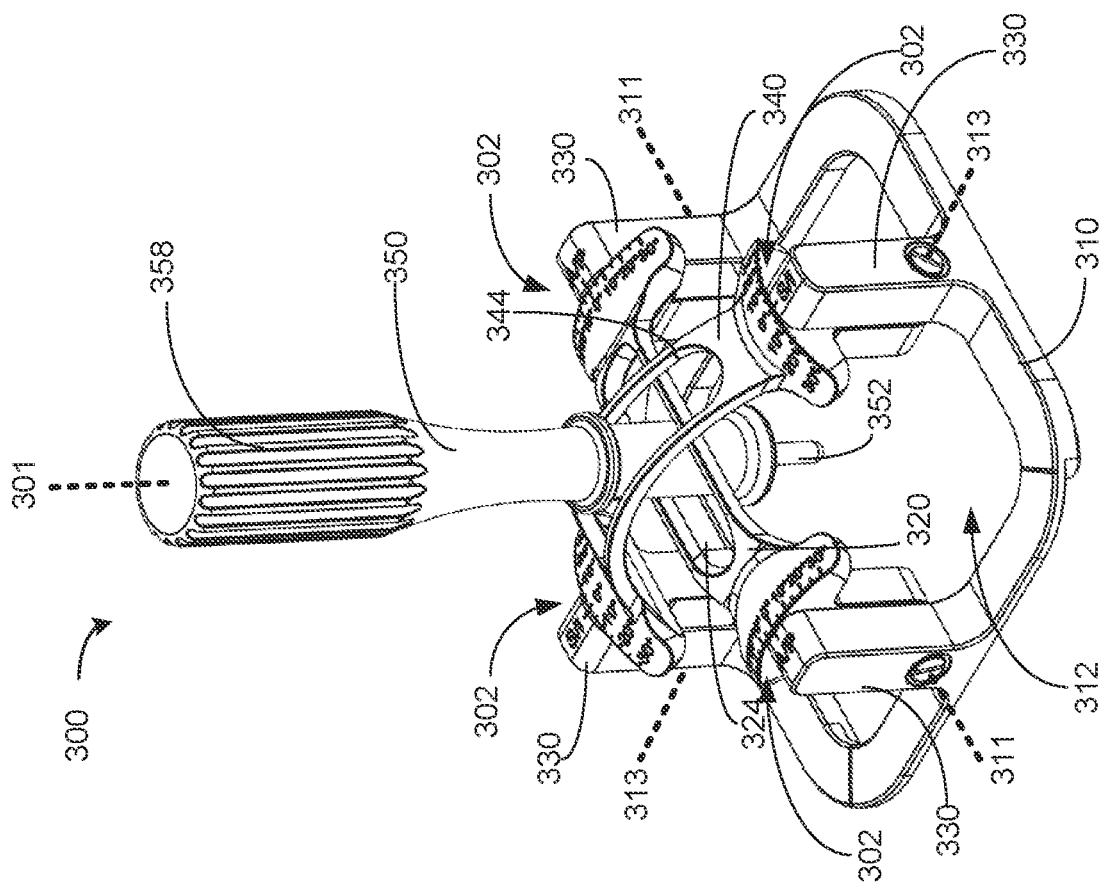
FIG. 9 is a perspective view of a drill guide adjuster, according to an example embodiment.

Referring now to FIGS. 9 and 10, perspective views of the adjustment device 300 are shown, according to an example embodiment. The adjustment device 300 is configured to lock or unlock the surgical guide 100. The adjustment device 300 is further configured to adjust a drill guide angle of the surgical guide 100 while the surgical guide 100 is unlocked. The adjustment device 300 includes a base 310 that defines an adjustment base plane. For example, the base 310 may include a bottom surface 314 (see FIG. 10) that defines an adjustment base plane. The base 310 further defines a base cavity 312 configured to receive a portion of the adjustment stand 500 to restrict movement between the adjustment device 300 and the adjustment stand 500 while the adjustment device 300 is positioned on top of the adjustment stand 500.

The adjustment device 300 further includes a plurality of projections 330 coupled to the base 310 and extending away from the bottom surface 314. The projections 330 define a plurality of apertures configured to each individually rotatably couple with a portion of a first adjustment track 320 or a second adjustment track 340, thereby coupling the first adjustment track 320 and the second adjustment track 340 to the base 310. The first adjustment track 320 is configured to rotate to rotate about a first axis 311 relative the base 310. For example, the first adjustment track 320 may rotate about the first axis 311 as a user of the adjustment device 300 sets a desired drill guide angle.

The first adjustment track 320 further includes a first adjustment track opening 324 extending through the first adjustment track 320. The first adjustment track opening 324 is configured to receive a portion of a drill guide adjuster 350 and allows a portion of the drill guide adjuster 350 to translate within the first adjustment track opening 324 as a user of the adjustment device 300 sets a desired drill guide angle. As shown, the first adjustment track opening 324 is generally linear in nature. For example, the first adjustment track opening 324 may extend in a direction parallel to the adjustment base plane.

The adjustment device 300 includes the second adjustment track 340. The second adjustment track 340 is rotatably coupled to two of the projections 330 and is configured to rotate about a second axis 313 relative the base 310. For example, the second adjustment track 340 may rotate about the second axis 313 as a user of the adjustment device 300 sets a desired drill guide angle, as is discussed further herein. The first axis 311 and the second axis 313 may be perpendicular one another and/or parallel the adjustment base plane. The second adjustment track 340 further includes a second adjustment track opening 344 extending through the second adjustment track 340. The second adjustment track opening 344 is configured to receive a portion of a drill guide adjuster 350 and allows a portion of the drill guide adjuster 350 to translate within the second adjustment track opening 344 as a user of the adjustment device 300 sets a desired drill guide angle. As shown, the second adjustment track opening 344 is generally arced in nature. For example, the second adjustment track opening 344 may extend at a curvature that defines a convex curvature relative the adjustment base plane.

The adjustment device 300 is shown to include a plurality of angular indicators 302. The angular indicators 302 may provide visual feedback to a user of the adjustment device 300 to allow them to properly orientate the drill guide angle of the surgical guide 100. For example, the angular indicators 302 may correspond with the drill guide angle of the surgical guide 100. For example, a first set of angular indicators 302 may indicate an angle of the drill guide 150 relative the base 110 within a first adjustment plane (e.g., corresponding with an angular orientation of the first track 120). Further, a second set of angular indicators 302 may indicate an angle of the drill guide 150 relative the based within a second adjustment plane (e.g., corresponding with an angular orientation of the second track 140).

The adjustment device 300 further includes the drill guide adjuster 350 coupled to the first adjustment track 320 and the second adjustment track 340. The drill guide adjuster 350 includes a handle 358 proximate a first end of the drill guide adjuster 350 and configured to be manipulated by a user of the adjustment device 300 as a user of the adjustment device 300 sets a desired drill guide angle.

Referring to FIG. 10, the drill guide adjuster 350 further includes an adjustment projection 352 proximate a second end of the drill guide adjuster 350. The adjustment projection 352 is configured to be inserted into the drill bore 152 (see FIGS. 1 and 2) such that manipulation of the handle 358 causes a change in the drill guide angle. The adjustment projection 352 extends from within an adjustment cavity 354 defined by the drill guide adjuster 350 proximate the second end of the drill guide adjuster 350. The adjustment cavity 354 is configured to receive the locking nut 170 (see FIG. 5) when the adjustment device 300 is positioned on top of the surgical guide 100. As the handle 358 is rotated, a plurality of splines 356 interface with the plurality of splines 172, thereby causing the locking nut 170 to rotate in response to the handle 358 being rotated to lock or unlock the surgical guide 100.

Figure 11:
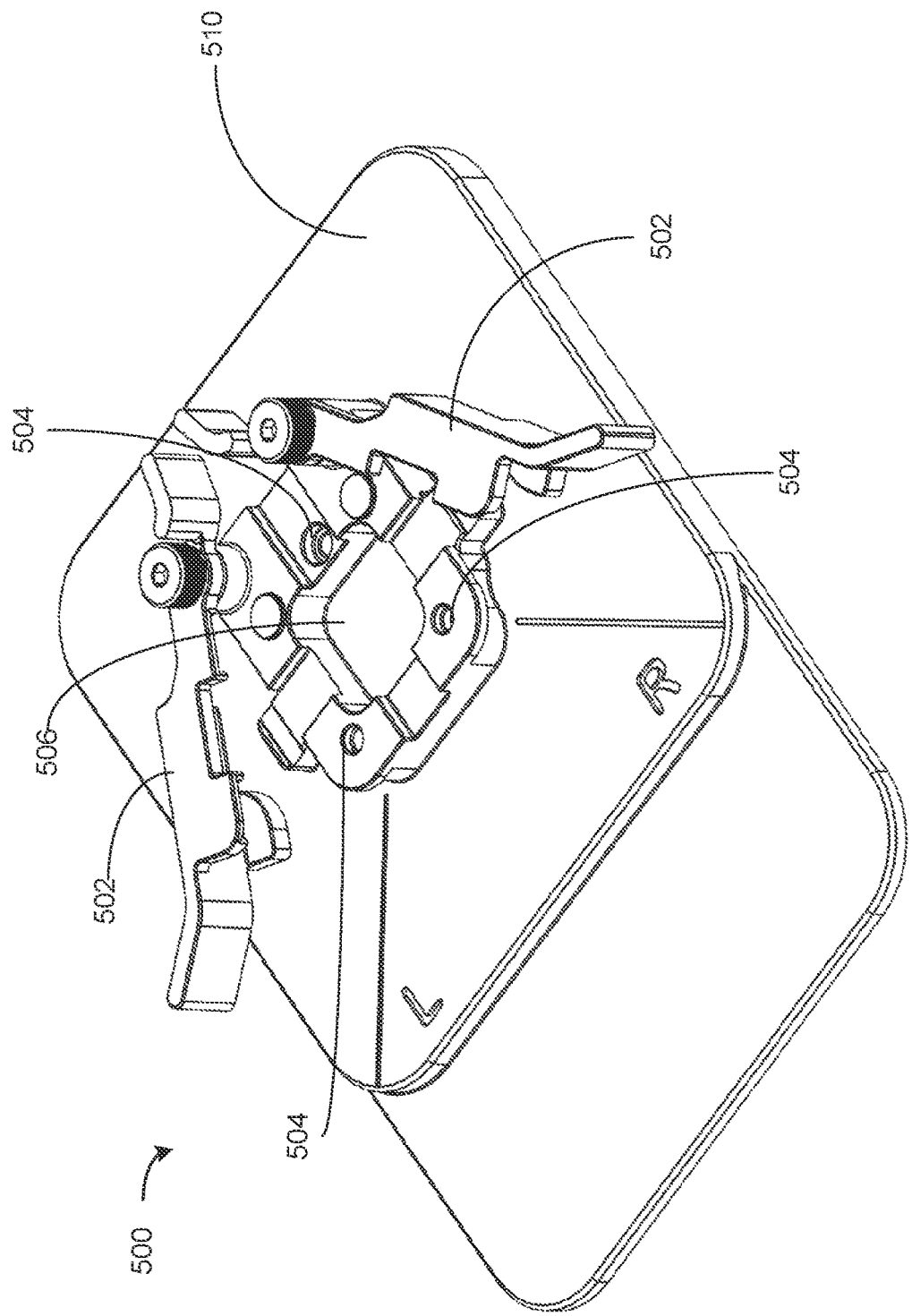
FIG. 11 is a perspective view of an adjustment stand, according to an example embodiment.

Referring now to FIG. 11, a perspective view of the adjustment stand 500 is shown, according to an example embodiment. The adjustment stand 500 is configured to receive and secure the adjustment device 300. As shown, the adjustment device 300 includes a stand base 510. The stand base 510 is configured to be positioned within the base cavity 312 of the adjustment device 300 to restrict relative movement between the adjustment stand 500 and the adjustment device 300.

The adjustment stand 500 further includes a guide cavity 506 defined by the stand base 510. The guide cavity 506 is configured to receive the adjustment device 300. The adjustment stand 500 further includes feet cavities 504 defined by the stand base 510. The feet cavities 504 are configured to individually receive the first foot 118, the second foot 118, and the third foot 118 (see FIG. 4) to restrict movement between the adjustment stand 500 and the surgical guide 100 while the surgical guide 100 is positioned within the guide cavity 506. Further, the adjustment stand 500 includes arms 502 configured to rotate to secure the surgical guide 100 to the adjustment stand 500 as discussed further herein.

Figure 12:
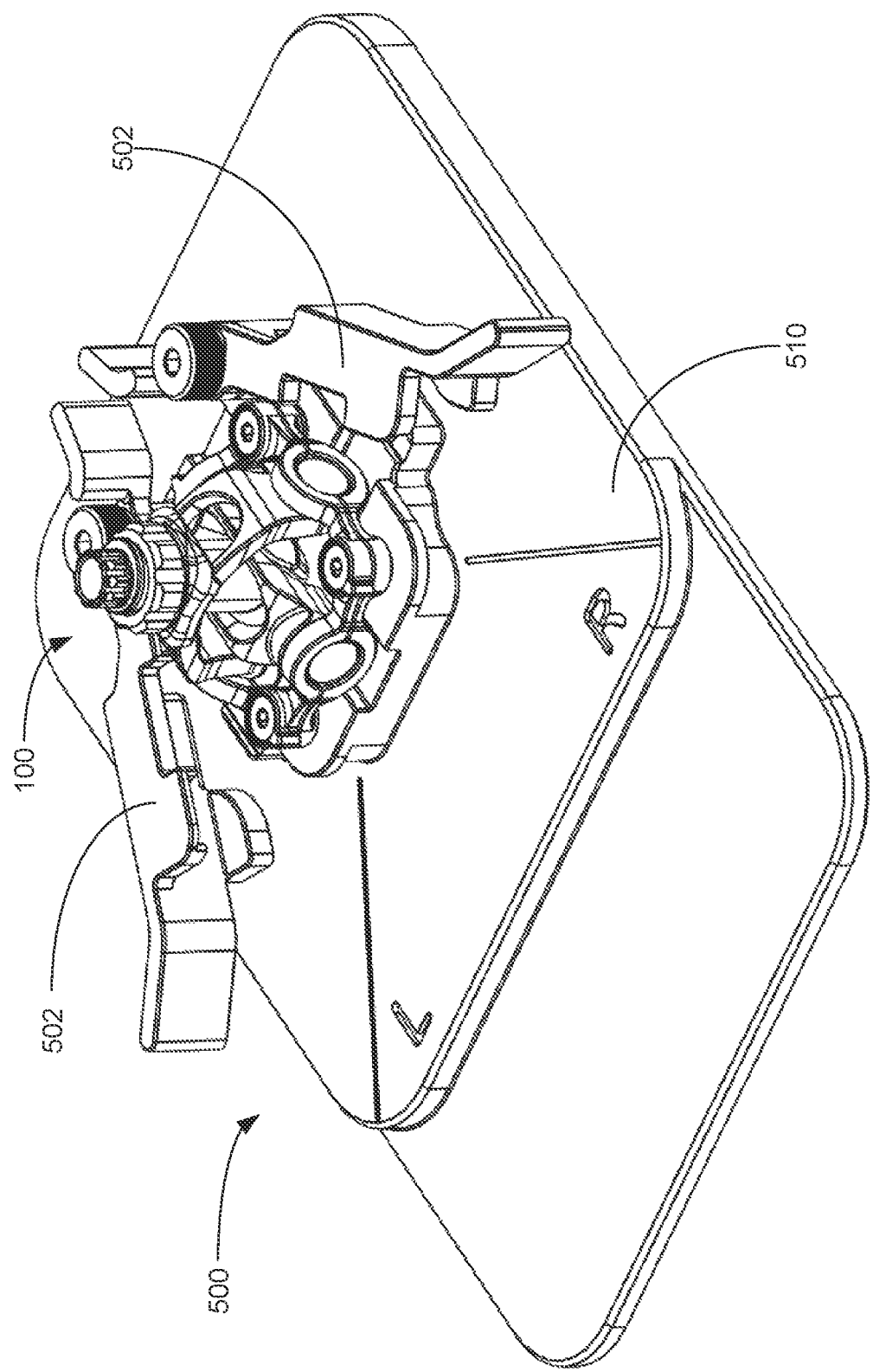
FIG. 12 is a perspective view of the surgical guide of FIG. 1 positioned on top of the adjustment stand of FIG. 11.

Referring now to FIG. 12, a perspective view of the surgical guide 100 positioned on top of the adjustment stand 500, according to an example embodiment. The arms 502 are in an open state such that the surgical guide 100 can placed within the guide cavity 506 and/or removed from the guide cavity 506.

Figure 13:
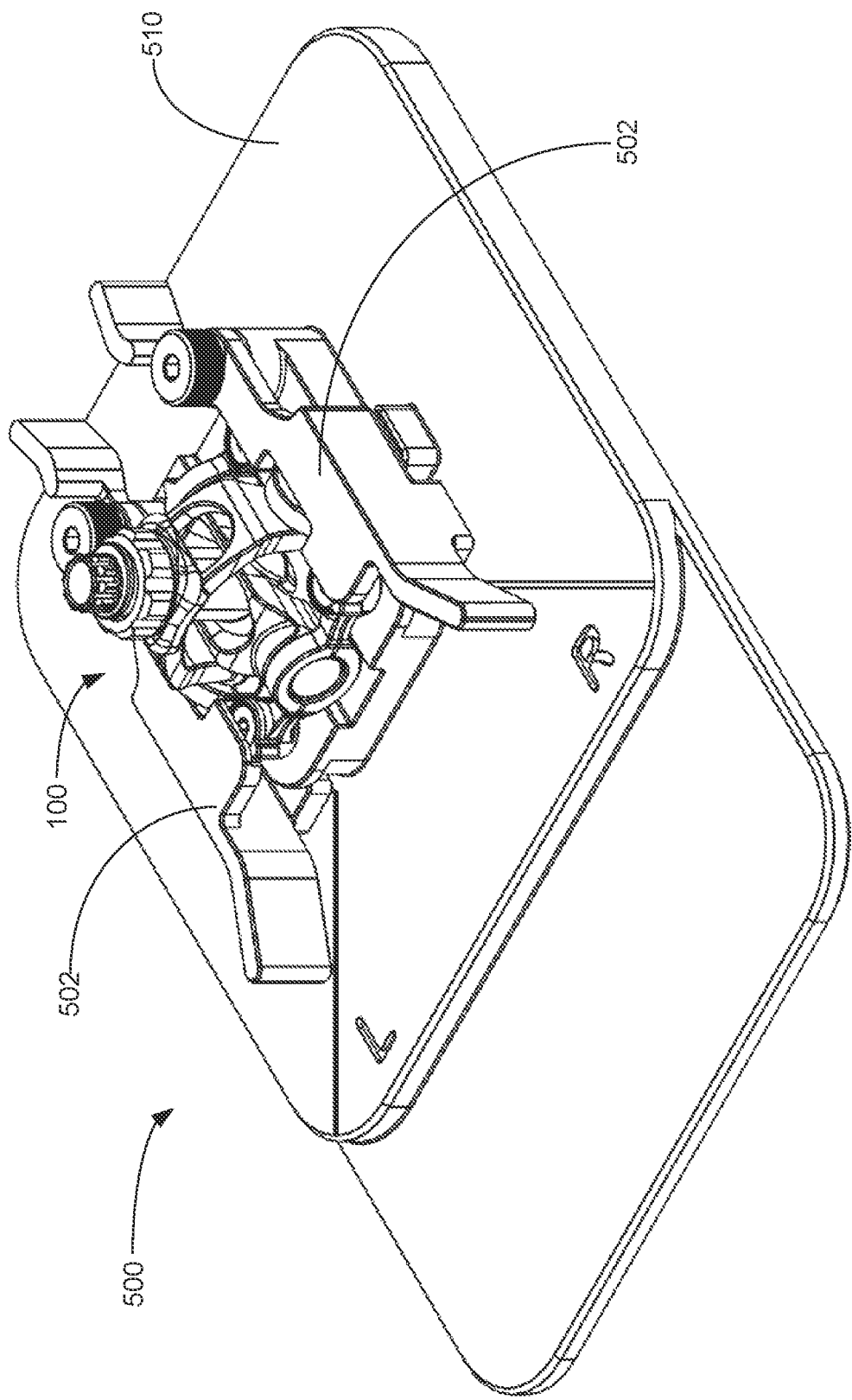
FIG. 13 is a perspective view of the surgical guide of FIG. 1 coupled to the adjustment stand of FIG. 11.

Referring now to FIG. 13 is a perspective view of the surgical guide of 100 coupled to the adjustment stand 500 is shown, according to an example embodiment. The arms 502 are in a closed state to restrict movement of the surgical guide 100 relative the adjustment stand 500. After the surgical guide 100 is coupled to the adjustment stand 500, the adjustment device 300 can be placed on top of the adjustment stand 500 and the adjustment projection 352 can be inserted into the drill bore 152 such that the adjustment device 300 can be used to adjust the drill guide angle of the surgical guide 100.

Figure 14:
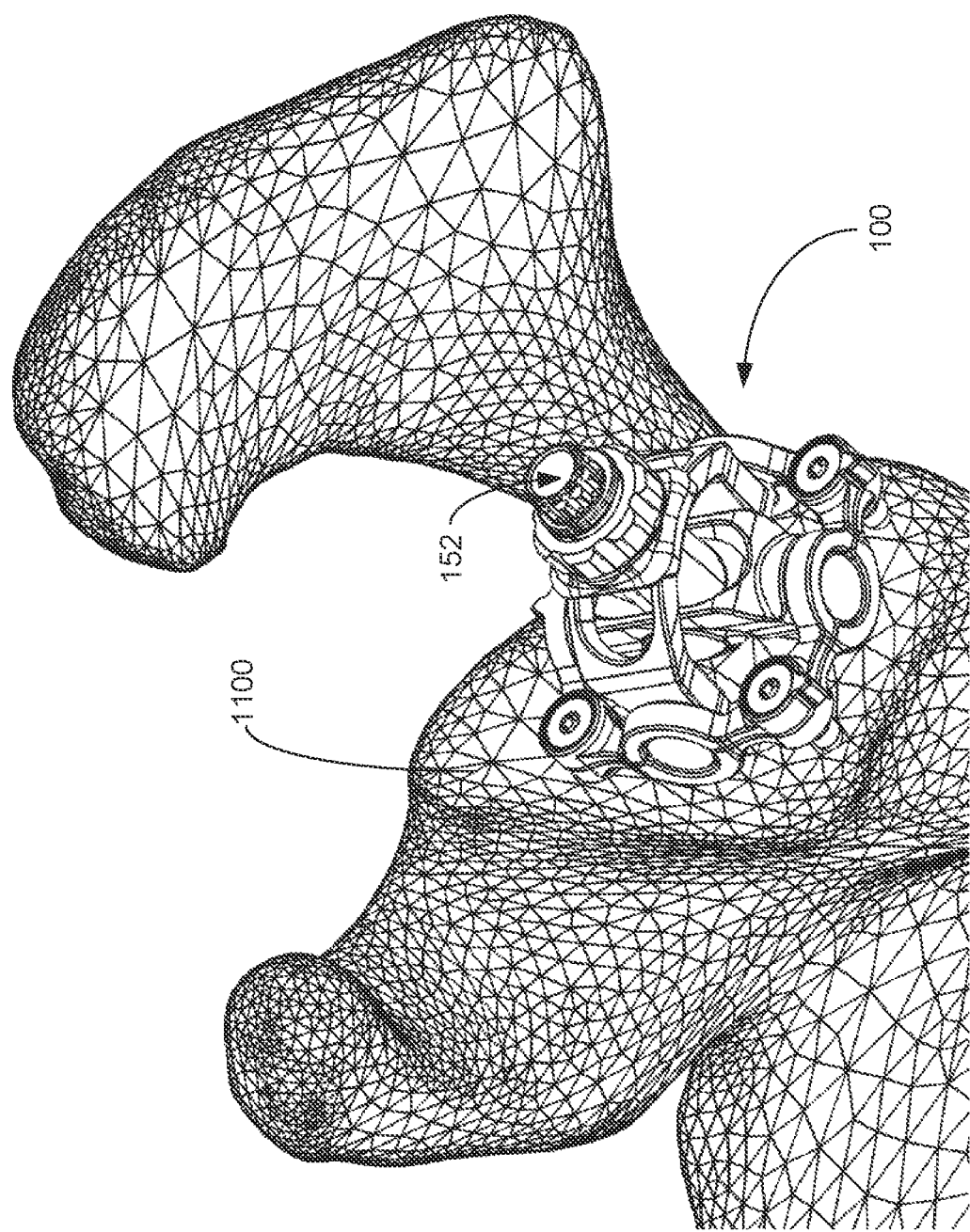
FIG. 14 is a perspective view of the drill guide of FIG. 1 positioned proximate a tissue, according to an example embodiment.

Referring now to FIG. 14, a perspective view of the surgical guide 100 positioned proximate a tissue 1100 is shown, according to an example embodiment. For example, the tissue 1100 may be a part of a shoulder bone and the surgical guide 100 may be positioned proximate the glenoid. The drill guide angle of the surgical guide 100 may be set at a desired angle such that a hole can be drilled through the drill bore 152 a predetermined angle (e.g., an optimal drill angle). For example, the surgical guide 100 may be used during a shoulder arthroplasty or a shoulder replacement surgery.

Figure 15:
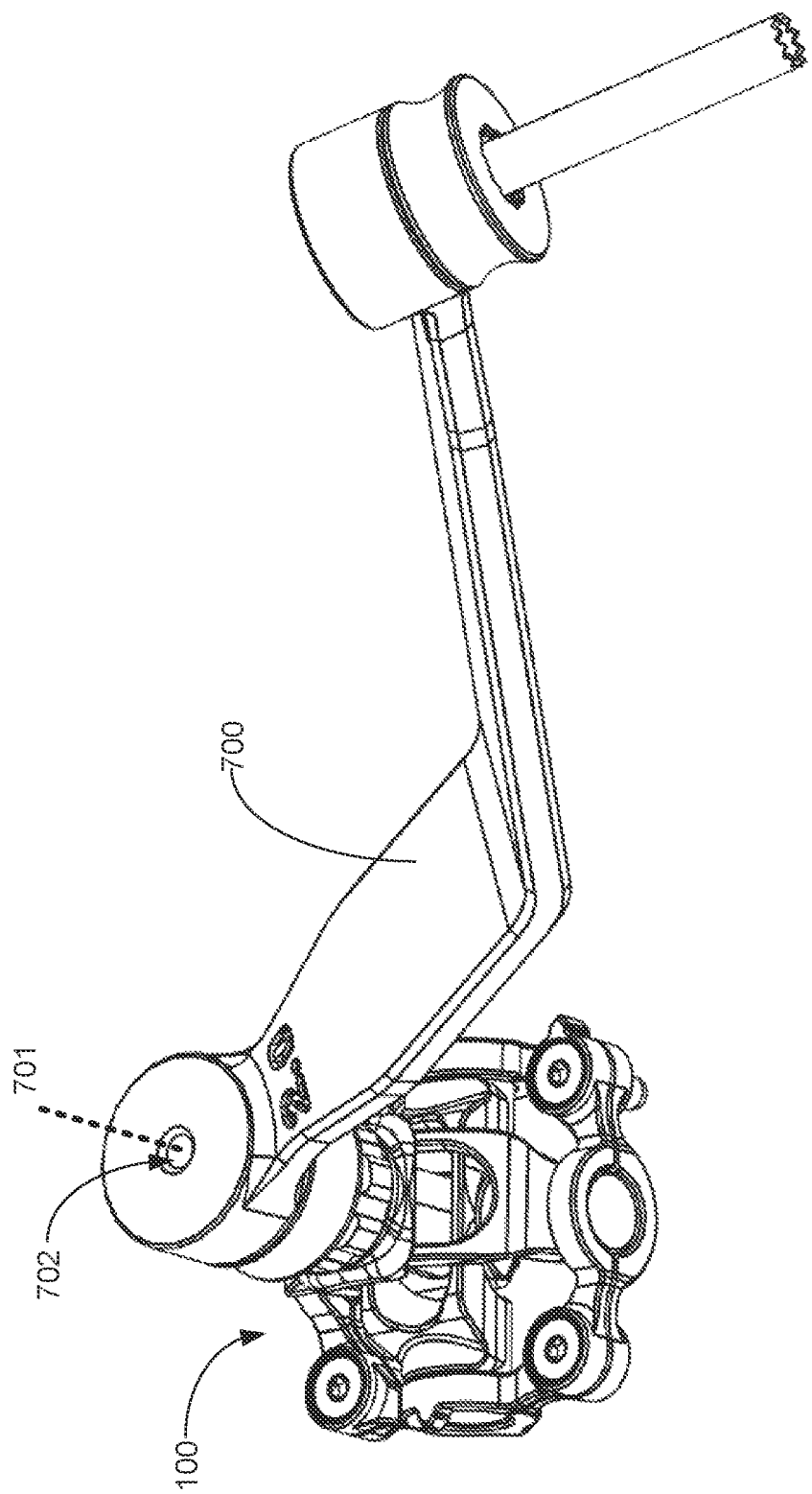
FIG. 15 is a perspective view of a drill guide retainer coupled to the drill guide of FIG. 1, according to an example embodiment.

Referring now to FIG. 15 is a perspective view of a drill guide retainer 700 (e.g., a drill guide with a handle) coupled to the surgical guide 100 is shown, according to an example embodiment. As discussed further herein, the surgical guide 100 includes an adapter 180 (see FIG. 5) configured to couple the drill guide to the drill guide retainer 700. The drill guide retainer 700 includes a retainer opening 702 extending along a retainer opening axis 701. The retainer opening axis 701 may alight with the bore axis 15 (see FIGS. 1 and 2)

when the drill guide retainer 700 is coupled to the surgical guide 100. The drill guide retainer is configured to further guide the drill bit through the retainer opening and the drill bore 152 (see FIGS. 1 and 2) to create a hole in tissue of a subject. Further, the drill guide retainer 700 may reduce a cross section of the drill bore 152 such that a smaller diameter hole can be drilled using the surgical guide 100. As shown, the drill guide retainer 700 is a 2.0 mm drill guide retainer. It should be appreciated that other size drill guide retainers may be used (e.g., 1 mm, 1.5 mm, 2.5 mm, 3 mm, 3.5 mm, etc.).

Figure 16:
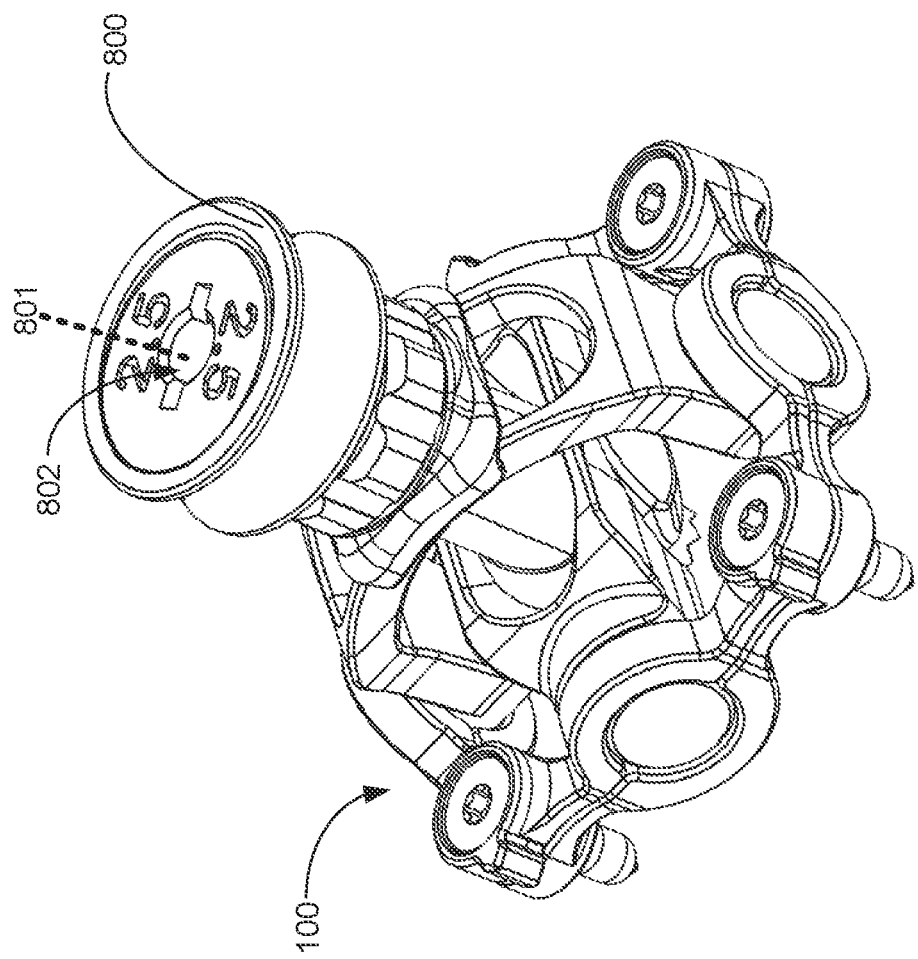
FIG. 16 is a perspective view of another drill guide retainer coupled to the drill guide of FIG. 1, according to an example embodiment.

Referring now to FIG. 16 is a perspective view of a drill guide retainer 800 (e.g., a drill guide without a handle) coupled to the surgical guide 100 is shown, according to an example embodiment. As discussed further herein, the surgical guide 100 includes an adapter 180 (see FIG. 5) configured to couple the drill guide to the drill guide retainer 800. The drill guide retainer 800 includes a retainer opening 802 extending along a retainer opening axis 801. The retainer opening axis 801 may alight with the bore axis 15 (see FIGS. 1 and 2) when the drill guide retainer 800 is coupled to the surgical guide 100. The drill guide retainer is configured to further guide the drill bit through the retainer opening and the drill bore 152 (see FIGS. 1 and 2) to create a hole in tissue of a subject. Further, the drill guide retainer 800 may reduce a cross section of the drill bore 152 such that a smaller diameter hole can be drilled using the surgical guide 100. As shown, the drill guide retainer 800 is a 2.5 mm drill guide retainer. It should be appreciated that other size drill guide retainers may be used (e.g., 1 mm, 1.5 mm, 2.0 mm, 3 mm, 3.5 mm, etc.). While FIGS. 15 and 16 show the surgical guide 100 being used with a drill guide retainer, it should be appreciated that the surgical guide 100 may be used as a drill guide without a drill guide retainer.

Figure 17:
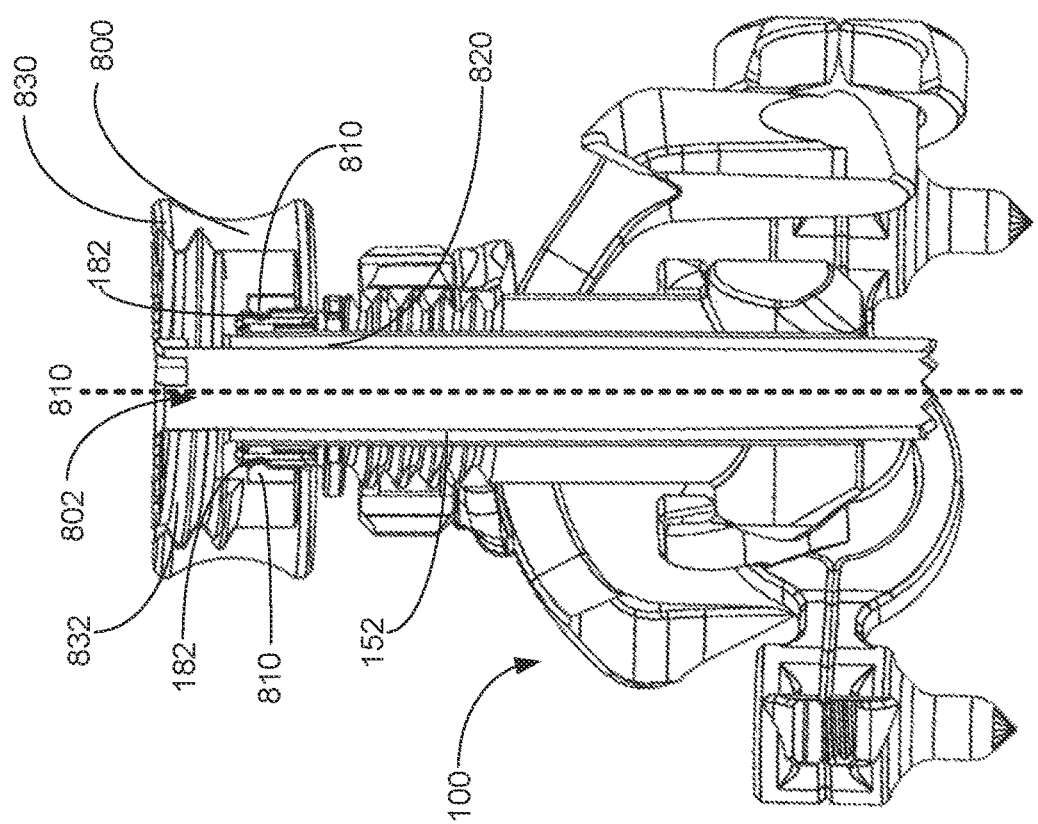
FIG. 17 is a cross sectional view of the drill guide retainer of FIG. 16 coupled to the drill guide of FIG. 1.

Referring now to FIG. 17, a cross sectional view of the drill guide retainer 800 coupled to the surgical guide 100 is shown, according to an example embodiment. The surgical guide 100 includes the indents 182 configured to individually receive a projection 810 of the drill guide retainer 800, thereby coupling the drill guide reducer to the surgical guide 100. For example, the interaction between the indents 182 and the projections 810 may create a snap fit between the drill guide retainer 800 and the indents 182.

According to the example embodiment shown, the drill guide reducer 800 includes a drill guide shaft 820 coupled to an outer ring 830. The drill guide shaft 820 is configured to be inserted into the drill guide bore 152 such that a hole can be drilled through the drill guide shaft 820. As discussed above, the outer ring 830 includes the projections 810 that create a snap fit between the drill guide retainer 800 and the indents 182. Further, the outer ring 830 includes threads 802 configured to couple with cannula threads.

Figure 18:
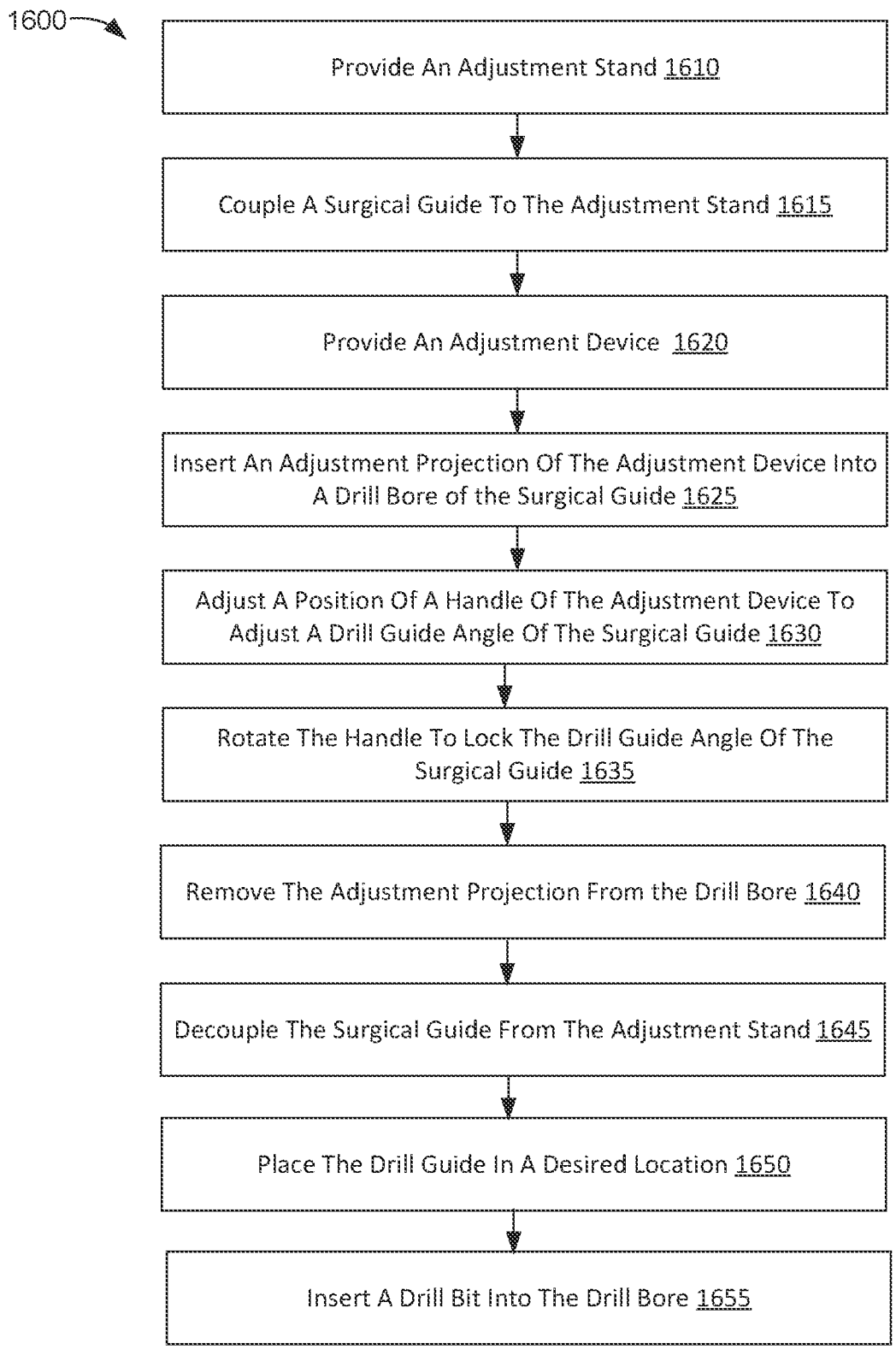
FIG. 18 is a block diagram illustrating a method of using the surgical guide of FIG. 1, according to an example embodiment.

Referring now to FIG. 18 is a block diagram illustrating a method of using the surgical guide 1600 is shown, according to an example embodiment. The method 1600 may utilize one or more of the components or devices described herein. It should be appreciated that the steps need not be performed in the order shown. Further, various steps may be omitted, and additional steps may be performed.

At step 1610, an adjustment stand is provided. For example, the adjustment stand 500 may be provided onto a flat surface. The adjustment stand 500 may be provided with the arms 502 in the open state (e.g., as shown in FIG. 11) such that a surgical guide may be placed on top of the adjustment stand.

At step 1615, a surgical guide is coupled to the adjustment stand. For example, the surgical guide 100 may be coupled to the adjustment stand 500. The surgical guide 100 may be placed on top of the adjustment stand 500 within the guide cavity 506 and the feet 118 may be positioned within the feet cavities 504 (e.g., as shown in FIG. 12). The arms 502 of the adjustment stand 500 may then be rotated to a closed state to couple the surgical guide 100 to the adjustment stand 500 (e.g., as shown in FIG. 13)

At step 1620, an adjustment device is provided. For example, the adjustment device 300 may be provided above the adjustment stand (e.g., as shown in FIG. 8).

At step 1625, an adjustment projection of the adjustment device is inserted into a drill bore of the surgical guide. For example, the adjustment projection 352 of the adjustment device 300 may be provided within the drill bore 152 of the surgical guide 100 (e.g., as shown in in FIG. 7). Further, step 1625 may include positioning the stand base 510 within the base cavity 312 of the adjustment device 300 to restrict relative movement between the adjustment stand 500 and the adjustment device 300.

At step 1630, a position of a handle of the adjustment device is adjusted to adjust a drill guide angle of the surgical guide. For example, a user of the adjustment device 300 may manipulate the handle 358, thereby causing a change in the drill guide angle. The user may utilize the angular indicators 302 to provide visual feedback to the user of the adjustment device 300 to allow the user to properly orientate the drill guide angle of the surgical guide 100. For example, the angular indicators 302 may correspond with the drill guide angle of the surgical guide 100. It should be appreciated that step 1630 may further involve rotating the handle 358 to transition the surgical guide 100 to the unlocked state.

At step 1635, the handle of the adjustment device is rotated to lock the drill guide angle of the surgical guide. For example, the handle 358 may be rotated, thereby causing the locking nut 170 to rotate in response to the handle 358 being rotated to lock the surgical guide 100. Once the surgical guide is in the locked state, the drill guide angle may be fixed.

At step 1640, the adjustment projection is removed from the drill bore. For example, the adjustment device 300 may be pulled off the top of the surgical guide, thereby removing the adjustment projection 352 from the drill bore 152.

At step 1645, the surgical guide is decoupled from the adjustment stand. For example, the arms 502 of the adjustment stand 500 may then be rotated to an open state such that the surgical guide 100 can be removed from the adjustment stand 500.

At step 1650 the drill guide is placed in a desired location. For example, the surgical guide 100 may be positioned proximate the tissue 1100 (e.g., as shown in FIG. 14).

At step 1655, a drill bit is inserted into the drill bore. For example, a drill bit may be inserted into the drill bore 152 and a hole may be drilled in the tissue 1100.

As utilized herein with respect to structural features (e.g., to describe shape, size, orientation, direction, relative position, etc.), the terms "approximately," "about," "substantially," and similar terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above.

It is important to note that any element disclosed in one embodiment may be incorporated or utilized with any other embodiment disclosed herein. The devices, systems and methods described herein may be embodied in other specific forms without departing from the characteristics thereof. The foregoing implementations are illustrative rather than limiting of the described systems and methods. The scope of the systems and methods described herein is thus indicated by the appended claims, rather than the foregoing description, and changes that come within the meaning and range of equivalency of the claims are embraced therein.

What is claimed is:

1. A surgical guide, comprising:
   a base;
   a drill guide coupled to the base, the drill guide including a drill guide body defining a drill bore configured to receive a drill bit and extending through the drill guide, the drill guide being configured to translate relative to the base to adjust a drill guide angle defined by the drill bore and the base, the drill guide further being configured to transition between a locked state and an unlocked state, wherein the drill guide angle is fixed in the locked state and the drill guide angle is adjustable in the unlocked state wherein the base includes a first foot including a first foot end, a second foot including a second foot end, and a third foot including a third foot end, wherein a base plane is defined by the first foot end, the second foot end, and the third foot end, the drill guide angle being defined by the drill bore and the base plane;
   a first track coupled to the base and defining a first track opening; and
   a second track coupled to the base and defining a second track opening, wherein the drill guide is configured to translate relative to the base within the first track opening and the second track opening;
   wherein the drill guide includes a locking nut configured to rotate relative to the drill bore, wherein rotation of the locking nut causes the drill guide to transition between the locked stated and the unlocked state;
   wherein the drill guide further includes a clamping member, wherein the rotation of the locking nut in a first direction causes the clamping member to compress against the second track to secure the drill guide in the locked state;
   wherein the drill guide further includes a first projection and a second projection extending from an outer portion of the drill guide body, wherein the rotation of the locking nut in the first direction causes the first projection and the second projection to compress against the first track to secure the drill guide in the locked state.

2. The surgical guide of claim 1, wherein the first track is rotatably coupled to the base and configured to rotate about a first axis.

3. The surgical guide of claim 2, wherein the first axis is parallel to the base plane.

4. The surgical guide of claim 3, wherein the second track is rotatably coupled to the base and configured to rotate about a second axis.

5. The surgical guide of claim 4, wherein the second axis is perpendicular to the first axis.

6. The surgical guide of claim 5, wherein the first axis and the second axis are parallel to the base plane.

7. The surgical guide of claim 1, wherein the second track opening is a curved opening defining a convex curvature relative to the base plane.

8. The surgical guide of claim 1, wherein the drill guide includes an adapter proximate a first end of the drill guide body, the adapter configured to receive a drill guide retainer.

9. The surgical guide of claim 8, wherein the adapter includes a plurality of spines surrounding an outer portion of the drill guide body.

10. A surgical system, comprising:
    a surgical guide, comprising:
      a base; and
      a drill guide coupled to the base, the drill guide including a drill guide body defining a drill bore configured to receive a drill bit and extending through the drill guide, the drill guide being configured to translate relative to the base to adjust a drill guide angle defined by the drill bore and the base, the drill guide further being configured to transition between a locked state and an unlocked state, wherein the drill guide angle is fixed in the locked state and the drill guide angle is adjustable in the unlocked state;
    an adjustment device configured to cause a change in the drill guide angle, comprising:
      an adjustment base configured to support the surgical guide; and
      a drill guide adjuster configured to engage the adjustment base, the drill guide adjuster including a handle proximate a first drill guide adjuster end of the drill guide adjuster, an adjustment projection proximate a second drill guide adjuster end of the drill guide adjuster, and a drill guide adjuster body positioned between the handle and the adjustment projection, the adjustment projection configured to be received within the drill bore such that movement of the handle causes a change in the drill guide angle; and an adjustment stand configured to selectively couple to the surgical guide, wherein the adjustment base is configured to receive at least a portion of the adjustment stand to limit relative movement between the adjustment base and the adjustment stand.

11. The surgical system of claim 10, wherein the drill guide adjuster further comprises:
a first adjustment track coupled to the adjustment base and defining a first adjustment track opening; and
a second adjustment track coupled to adjustment body and defining a second adjustment track opening, wherein movement of the handle causes the drill guide adjuster to translate within at least one of the first adjustment track opening or the second adjustment track opening.

12. The surgical system of claim 11, wherein the first adjustment track is rotatably coupled to the adjustment base and configured to rotate about a first adjustment axis.

13. The surgical system of claim 12, wherein the first adjustment axis is parallel to a base plane defined by the base while the drill guide adjuster and the drill guide are coupled to the adjustment stand.

14. The surgical system of claim 12, wherein the second adjustment track is rotatably coupled to the adjustment base and configured to rotate about a second adjustment axis.

15. The surgical system of claim 14, wherein the second adjustment axis is perpendicular to the first adjustment axis.

16. The surgical system of claim 15, wherein rotation of the handle is configured to cause the drill guide to transition between the locked state and the unlocked state while the drill guide adjuster is coupled to the drill guide.

17. The surgical system of claim 16, wherein the drill guide includes a locking nut configured to rotate relative to the drill bore, wherein the rotation of the locking nut causes the drill guide to transition between the locked stated and the unlocked state.

18. The surgical system of claim 17, wherein the locking nut includes a plurality of locking nut splines and the drill guide adjuster body includes a plurality of drill guide adjuster body splines configured to interface with the plurality of locking nut splines while the drill guide adjuster is coupled to the drill guide such that the rotation of the handle is configured to cause the drill guide to transition between the locked state and the unlocked state.

19. The surgical system of claim 11, wherein the adjustment base defines an adjustment base plane and the drill guide adjuster includes a first adjustment track indicator configured to indicate a first relative angular orientation of the drill guide in a first adjustment plane relative to the adjustment base plane.

20. The surgical system of claim 19, wherein the drill guide adjuster includes a second adjustment track indicator configured to indicate a second relative angular orientation of the drill guide in a second adjustment plane relative to the adjustment base.

21. The surgical system of claim 11, wherein the adjustment stand includes a first clamping arm and a second clamping arm configured to selectively couple to the surgical guide to the adjustment stand.

22. A method, comprising:
providing an adjustment stand;
coupling a surgical guide to the adjustment stand, the surgical guide comprising:
a base; and
a drill guide coupled to the base, the drill guide including a drill guide body defining a drill bore and extending through the drill guide, the drill bore and the base defining a drill guide angle;
providing an adjustment device, comprising:
an adjustment base;
a drill guide adjuster coupled to the base, the drill guide adjuster including a handle proximate a first drill guide adjuster end of the drill guide adjuster, an adjustment projection proximate a second drill guide adjuster end of the drill guide adjuster, and a drill guide adjuster body positioned between the handle and the adjustment projection;
inserting the adjustment projection into the drill bore;
adjusting a position of the handle thereby causing the drill guide to translate relative to the base to adjust the drill guide angle; and
locking the drill guide such that the drill guide angle is fixed.

23. The method of claim 22, further comprising:
removing the adjustment projection from the drill bore;
decoupling the drill guide from the adjustment stand; and
providing the drill guide in a desired location proximate a bone.

24. The method of claim 22, further comprising rotating the handle while the adjustment projection is positioned within the drill guide causing the drill guide to transition to a locked state to prevent change in the drill guide angle.

25. A surgical guide, comprising:
a base;
a drill guide coupled to the base, the drill guide including a drill guide body defining a drill bore configured to receive a drill bit and extending through the drill guide, the drill guide being configured to translate relative to the base to adjust a drill guide angle defined by the drill bore and the base, the drill guide further being configured to transition between a locked state and an unlocked state, wherein the drill guide angle is fixed in the locked state and the drill guide angle is adjustable in the unlocked state wherein the base includes a first foot including a first foot end, a second foot including a second foot end, and a third foot including a third foot end, wherein a base plane is defined by the first foot end, the second foot end, and the third foot end, the drill guide angle being defined by the drill bore and the base plane;
a first track coupled to the base and defining a first track opening; and
a second track coupled to the base and defining a second track opening, wherein the drill guide is configured to translate relative the base within the first track opening and the second track opening;
wherein the first track opening is a linear opening extending in a direction parallel to the base plane.

* * * * *